United States Patent
Hixson (10) Patent No.: US 11,327,081 B2
(45) Date of Patent: May 10, 2022

(54) CALIBRATORS AND CONTROLS FOR THE DETERMINATION OF PERCENT GLYCATED HEMOGLOBIN IN A PATIENT'S LIQUID TEST SAMPLE

(71) Applicant: Siemens Healthcare Diagnostics Inc., Tarrytown, NY (US)

(72) Inventor: Craig Hixson, Bear, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 17/310,137

(22) PCT Filed: Jan. 17, 2020

(86) PCT No.: PCT/US2020/014014
§ 371 (c)(1),
(2) Date: Jul. 20, 2021

(87) PCT Pub. No.: WO2020/167411
PCT Pub. Date: Aug. 20, 2020

(65) Prior Publication Data
US 2022/0043009 A1  Feb. 10, 2022

Related U.S. Application Data (60) Provisional application No. 62/806,163, filed on Feb. 15, 2019.

(51) Int. Cl.
*G01N 33/72* (2006.01)

(52) U.S. Cl.
CPC ....... *G01N 33/723* (2013.01); *G01N 2440/38* (2013.01)

(58) Field of Classification Search
CPC ...... G01N 33/49; G01N 33/72; G01N 33/721; G01N 33/723; G01N 2440/38; G01N 21/274; Y10T 436/10; Y10T 436/105831; Y10T 436/25
USPC ............... 436/8, 15, 63, 66, 67, 174
See application file for complete search history.

(56) References Cited

U.S. PATENT DOCUMENTS

| | | | |
|---|---|---|---|
| 4,590,164 A | 5/1986 | Gain | |
| 5,589,393 A * | 12/1996 | Fiechtner | G01N 33/54353 356/42 |
| 6,043,043 A * | 3/2000 | Yip | G01N 33/723 422/68.1 |
| 8,431,415 B2 * | 4/2013 | Shigenobu | G01N 33/5306 436/534 |
| 2007/0224685 A1 | 9/2007 | Kouzuma et al. | |
| 2008/0096230 A1 | 4/2008 | Yuan et al. | |
| 2008/0102525 A1 * | 5/2008 | Rannikko | G01N 33/96 436/15 |
| 2011/0000788 A1 * | 1/2011 | Deschamps | G01N 27/44791 204/451 |
| 2014/0134597 A1 * | 5/2014 | Ebrahim | G01N 33/5094 435/2 |
| 2015/0093760 A1 | 4/2015 | Kim et al. | |
| 2018/0231544 A1 | 8/2018 | Brueckner et al. | |

FOREIGN PATENT DOCUMENTS

| | | |
|---|---|---|
| CN | 101023168 | 6/2007 |
| EP | 1304571 | 4/2003 |
| EP | 1314982 | 5/2003 |
| EP | 3550030 | * 10/2019 |
| JP | S59183370 | 10/1984 |
| JP | 406508690 | 9/1994 |
| JP | 2003344417 | 3/2003 |
| JP | 4950406 | 1/2004 |
| JP | 2011099777 | 5/2011 |
| JP | 4733335 | 7/2011 |
| WO | 1992022818 | 12/1992 |
| WO | 2006013921 | 2/2006 |
| WO | 2018065981 | 4/2018 |
| WO | 2018101389 | 6/2018 |

OTHER PUBLICATIONS

International Search Report for PCT/US2020/014014 dated Apr. 1, 2020.
Diabetes Care, vol. 38, Supp. 1, Jan. 2015, S8-16.
American Diabetes Association; Standards of Medical Care in Diabetes—2015 Abridged for Primary Care Providers Clinical Diabetes; Apr. 2015; vol. 33; No. 2; pp: 97-111.

* cited by examiner

*Primary Examiner* — Maureen Wallenhorst (57) ABSTRACT

Non-limiting embodiments of methodologies for preparing diagnostic assay(s) calibrator(s), calibration material(s), and/or control(s), as well as kits, devices, and method(s) of calibration related thereto.

14 Claims, 8 Drawing Sheets

D-glucose-hemoglobin + periodate ⟶ formic acid + formaldehyde + hemoglobin

Human: NH₂-Val-His-Leu-Thr-Pro-Glu-

Ovine, bovine, caprine: NH₂-Leu-Thr-Ala-Glu-Glu-Lys-

Equine: NH₂-Val-Gln-Leu-Ser-Gly-Glu-

Porcine: NH₂-Val-His-Leu-Ser-Ala-Glu-

FIG. 8

CALIBRATORS AND CONTROLS FOR THE DETERMINATION OF PERCENT GLYCATED HEMOGLOBIN IN A PATIENT'S LIQUID TEST SAMPLE

CROSS REFERENCE TO RELATED APPLICATIONS

Not Applicable.

STATEMENT REGARDING FEDERALLY FUNDED RESEARCH OR DEVELOPMENT

Not Applicable.

TECHNICAL FIELD

The presently disclosed and claimed inventive concept(s) relate to a device(s), kit(s), and method(s) that dispense at least one liquid, including, but not limited to, at least one liquid reagent(s) and/or buffer, for the conductance of at least one diagnostic assay. More specifically, the presently disclosed and claimed inventive concept(s) relate to non-limiting embodiments for the production of assay calibrators, calibration materials, and/or quality controls.

BACKGROUND

Numerous devices and methods exist for detecting analytes that may be present in a fluid sample. Such devices have been proven to be effective in diagnostic assays that detect the presence and quantity of certain analytes indicative of a patient's health, including, but not limited to, total hemoglobin, glycated hemoglobin (HbA1c), microalbumin and creatinine, and lipid-based analytes, such as cholesterol, triglycerides, and/or high-density lipoproteins.

The measurement of the percentage of glycated hemoglobin present in a patient's blood sample is indicative of the average plasma glucose concentration present within the patient's blood over a period of about the previous three months. As the average amount of plasma glucose increases at least a portion the hemoglobin in the patient's blood non-enzymatically converts to glycated hemoglobin, thereby resulting in an increase in the percentage or fraction of Hb1Ac present in the patient's blood (when compared to the total amount of hemoglobin present in the patient's blood).

However, when conducting diagnostic assays to detect the presence and/or concentration of at least one analyte of interest (for instance, by way of example, glycated hemoglobin (HbA1c)), measurement instruments must be calibrated to ensure that the results obtained are accurate. When the analyte of interest is glycated hemoglobin, it can be very difficult to construct calibrators that detect both extremely low levels (i.e., less than about 4% glycated hemoglobin) and/or extremely high levels (i.e., greater than about 12% glycated hemoglobin) of Hb1Ac present in a patient's liquid test sample (such as, by way of example, a patient's whole blood sample). Currently, it is common to seek out patients whose blood samples contain the desired levels (both low and high concentrations) of glycated hemoglobin. Once found, blood samples are taken from this demographic of patients and utilized to set the upper and lower thresholds for calibrators that detect both total hemoglobin and percent glycated hemoglobin.

While effective in setting the low and high thresholds for diagnostic calibrators, it is often times very difficult, if not impossible, to find an adequate number of patients whose blood samples contain the requisite low and high concentrations of glycated hemoglobin needed for optimizing the calibration thresholds. Accordingly, there is a need for improved methods that produce diagnostic assay calibrators that span the clinical assay range of percent glycated hemoglobin from very low (i.e., less than or equal to about 3%) to very high (i.e., greater than or equal to about 18%). It is to such methods, as well as devices and kits related thereto, that the presently disclosed and claimed inventive concept(s) is directed.

DETAILED DESCRIPTION

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the devices, kits, and/or methods disclosed and claimed herein can be made and executed without undue experimentation in light of the present disclosure. While the compositions and methods of this presently disclosed and claimed inventive concept(s) have been described in terms of preferred embodiments, it will be apparent to those of skill in the art that variations may be applied to the compositions and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more or greater numbers of compounds. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by ±20% or ±10%, or ±5%, or ±1%, or ±0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, the phrase "associated with" includes both direct association of two moieties to one another as well as indirect association of two moieties to one another. Non-limiting examples of associations include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety.

The term "analyte(s) of interest" as used herein refer to any material, compound, molecule, chemical, and/or protein that is desired by a user to be detected in a patient's liquid test sample via at least one diagnostic assay. In one non-limiting embodiment of the presently disclosed and/or claimed inventive concept(s), the analyte(s) of interest comprise or consist of total hemoglobin, glycated hemoglobin, and combinations thereof.

The term "liquid test sample" as used herein will be understood to include any type of biological fluid sample that may be utilized in accordance with the presently disclosed and claimed inventive concept(s). Examples of biological samples that may be utilized include, but are not limited to, whole blood or any portion thereof. As used herein, the term "volume" as it relates to the liquid test sample utilized in accordance with the presently disclosed and claimed inventive concept(s) means from about 0.1 microliter to about 100 microliters, or from about 1 microliter to about 75 microliters, or from about 2 microliters to about 60 microliters, or less than or equal to about 50 microliters. In one non-limiting embodiment of the presently disclosed and/or claimed inventive concept(s), the liquid test sample, is a volume of whole blood.

The term "patient" includes human and veterinary subjects. In certain embodiments, a patient is a mammal. In certain other embodiments, the patient is a human. "Mammal" for purposes of treatment refers to any animal classified as a mammal, including human, domestic and farm animals, nonhuman primates, and zoo, sports, or pet animals, such as dogs, horses, cats, cows, etc.

Turning now to particular embodiments, the presently disclosed and claimed inventive concept(s) relate to a device(s), kit(s), and method(s) for dispensing at least two liquid reagents for use in analyte(s) detection assays. More specifically, the presently disclosed and claimed inventive concept(s) relate to a modified apparatus present within a reaction cassette that is capable of dispensing at least two liquid reagents for use in analyte(s) detection assays, as well as kits and methods of use related thereto.

It is contemplated that virtually any reagent used in the fields of biological, chemical, or biochemical analyses and assays could be used in the devices, kits, and methods of the presently claimed and disclosed inventive concept(s). It is contemplated that these reagents may undergo physical and/or chemical changes when bound to an analyte of interest whereby the intensity, nature, frequency, or type of signal generated by the reagent-analyte complex is directly proportional or inversely proportional to the concentration of the analyte existing within the fluid sample. These reagents may contain indicator dyes, metal, enzymes, polymers, antibodies, and electrochemically reactive ingredients and/or chemicals that, when reacting with an analyte(s) of interest, may exhibit change in color.

Any method of detecting and measuring the analyte in a liquid test sample can be used in the devices, kits, and methods of the presently claimed and inventive concepts. A variety of assays for detecting analytes are well known in the art and include, but are not limited to, chemical assays, enzyme inhibition assays, antibody stains, latex agglutination, latex agglutination inhibition and immunoassays, such as, radioimmunoassays, chemiluminescent immunoassays, electrochemiluminescent immunoassays, enzyme immunoassays, and fluoroimmunoassays. The term "antibody" herein is used in the broadest sense and refers to, for example, intact monoclonal antibodies, polyclonal antibodies, multi-specific antibodies (e.g., bispecific antibodies), and to antibody fragments that exhibit the desired biological activity (e.g., antigen/analyte-binding). The antibody can be of any type or class (e.g., IgG, IgE, IgM, IgD, and IgA) or sub-class (e.g., IgG1, IgG2, IgG3, IgG4, IgA1, and IgA2).

While immunoassays (including, but not limited to, sequential analytical chemical and immunoassays) may be utilized for the detection of at least one analyte of interest present in a liquid test sample, a person having ordinary skill in the art should readily understand that the presently disclosed and claimed inventive concept(s) are not strictly limited to immunoassays and may include, by way of example and not by limitation, chemical and chemical-based assays, nucleic acid assays, lipid-based assays, and serology-based assays. Immunoassays, including radioimmunoassays and enzyme-linked immunoassays, are useful methods for use with the presently claimed and disclosed inventive concepts. A variety of immunoassay formats, including, for example, competitive and non-competitive immunoassay formats, antigen/analyte capture assays and two-antibody sandwich assays can be used in the methods of the invention. Enzyme-linked immunosorbent assays (ELISAs) and phenylboronate affinity methods can be used in the presently claimed and disclosed inventive concepts, as well. In the case of an enzyme immunoassay, an enzyme is typically conjugated to at least one antibody, generally by means of glutaraldehyde, periodate, hetero-bifunctional crosslinking agents, or biotin-streptavidin complexes. As will be readily recognized, however, a wide variety of different conjugation techniques exist which are readily available for use with the presently disclosed and claimed inventive concept(s) to one skilled in the art.

Assays, including, but not limited to, immunoassays, nucleic acid capture assays, lipid-based assays, and serology-based assays, can be developed for a multiplexed panel of proteins, peptides, lipids, drugs, and nucleic acids which may be contained within a liquid test sample, with such proteins and peptides including, for example but not by way of limitation, albumin, microalbumin, cholesterol, triglycerides, high-density lipoproteins, low-density lipoproteins, hemoglobin, myoglobin, α-1-microglobin, immunoglobulins, enzymes, proteins, glycoproteins, protease inhibitors, drugs, cytokines, creatinine, and glucose. The device(s), kit(s), and method(s) disclosed and/or claimed herein may be used for the analysis of any fluid sample, including, without limitation, whole blood, plasma, serum, or urine.

Glycated hemoglobin (Hb1Ac) is a form of hemoglobin that is measured primarily to identify the average glucose concentration present in a patient's liquid test sample (for instance, by way of example, a patient's whole blood sample) over a period of time. Glycated hemoglobin is formed by a non-enzymatic mechanism resulting from the exposure of hemoglobin to plasma glucose. As the average amount of glucose increases over time, the percent of glycated hemoglobin also increases. This relationship allows for glycated hemoglobin to serve as a marker for average blood glucose level of a patient over a period of (usually) two to three months prior to the hemoglobin specimen collection. For individuals without diabetes mellitus, the normal range for glycated hemoglobin is less than about 5.6% of the total hemoglobin count. Glycated hemoglobin levels greater than 5.6% and less than about 6.4% of the total hemoglobin count are indicative of an increased risk of diabetes, while glycated hemoglobin levels of greater than about 6.4% of total hemoglobin count suggests the presence of diabetes. Due to the severity of complications caused by the presence of diabetes, it is clinically desirable to manage the glycated hemoglobin levels to less than about 7% of the total hemoglobin count in a patient suffering from this disease. The use of glycated hemoglobin as a diagnostic criterion for diabetes and pre-diabetes provides several advantages in comparison to either fasting plasma glucose levels or oral glucose overload, including: (i) a better index of overall glycemic exposure; (ii) increased structural stability; and (iii) less variability caused by, for instance, prandial status and/or acute stress.

Figure 1:
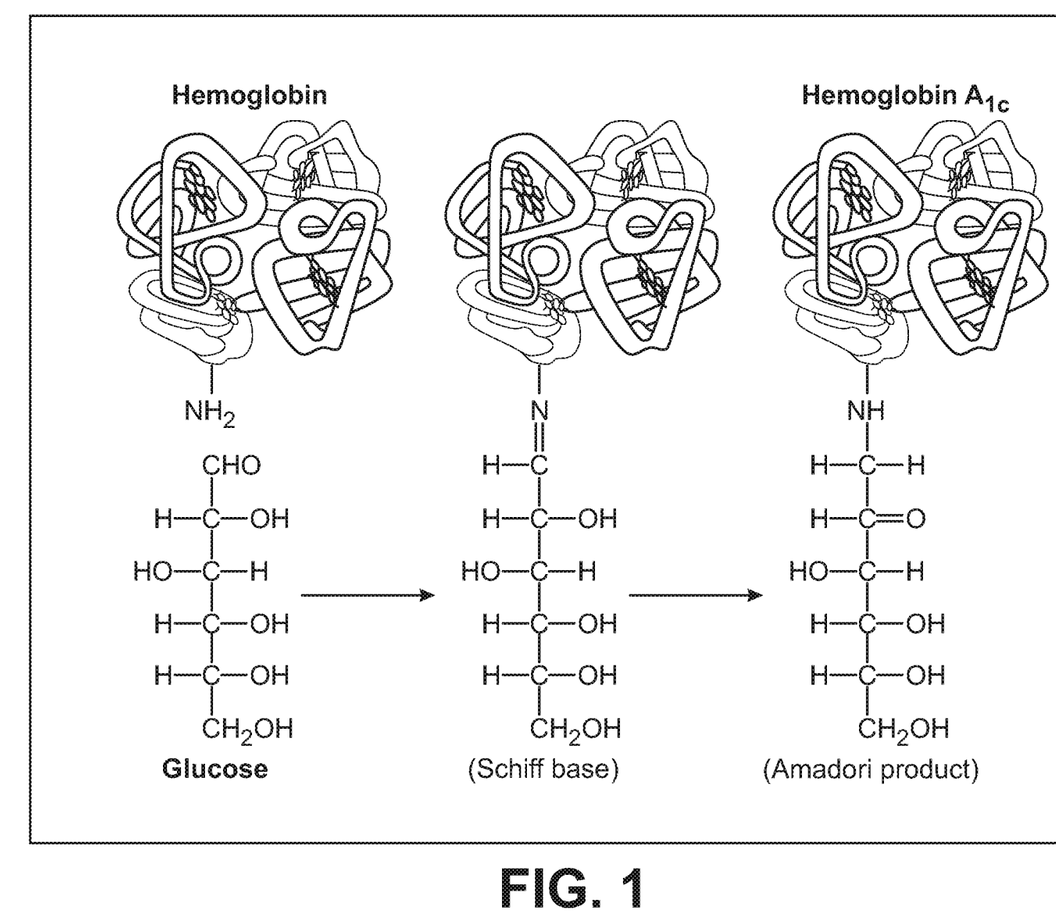
FIG. 1 is a schematic diagram of hemoglobin subunits conjugated with glucose.

Glycated hemoglobin is a protein molecule in which the N-terminal valine residue of the β-subunit of hemoglobin has been modified by blood glucose. As shown in greater detail in FIG. 1, this modification is the result of, for instance, the non-enzymatic reaction of glucose with free α-groups, proceeding through a Schiff case intermediate (aldimine) to produce a relatively stable ketoamine product.

Assays that measure glycated hemoglobin present in a patient's blood sample require periodic calibration to ensure that the results obtained are clinically accurate. Calibrators are standard or reference materials with a known concentration which are utilized to standardize or calibrate a diagnostic procedure and/or instrument. Control materials are employed to ensure that the diagnostic assay procedure and/or instrumentation is operating properly.

Calibrators and/or calibration materials are typically run at pre-defined intervals of time and when there are changes and/or alterations in the diagnostic assay instrumentation, such as, by way of example only, during instrument servicing, when reagent lots are changed, or whenever the results obtained from the diagnostic assay(s) appear questionable and/or out of clinical range. The performance of diagnostic assay to identify an analyte(s) of interest can be monitored and/or calculated by analyzing the calibrator(s) and/or calibration material(s) and then comparing the observed values obtained from the test sample to the known values of the calibrator(s) and/or calibration material(s). The known values are represented by a range of acceptable values and/or upper and/or lower limits for the calibrator(s) and/or calibration material(s). When the values obtained from a patient's liquid test sample resulting from the conductance of at least one diagnostic assay fall within the control limits, a user can be assured that the results obtained from the analytical method and/or diagnostic assay is functioning properly. However, when the observed results fall outside the control limits, a user should be alerted that the analytical results obtained may be inaccurate. When preparing calibrators, calibration materials, and controls, such calibrators, calibration materials, and controls should be as close in composition as possible to the specimens being assayed as they are employed to monitor the reliability of a diagnostic procedure(s) and/or instrument(s) and to minimize, if not eliminate, the reporting of incorrect test results.

As previously mentioned herein, one aspect of the presently disclosed and/or claimed inventive concept(s) involves both improved method(s) for preparing calibrators, calibration materials, and/or controls for the determination of percent glycated hemoglobin present in a patient's liquid test sample, as well as improved method(s) of calibration. Such improved calibrators and method(s) related thereto allow calibration of diagnostic assay procedures and/or instrumentation that spans the clinical assay of percent glycated hemoglobin from very low (such as, by way of example only, less than or equal to about 3% glycated hemoglobin) to very high (such as, by way of example only, greater than or equal to about 18% glycated hemoglobin).

In one non-limiting embodiment of the presently disclosed and/or claimed inventive concept(s), the percent of glycated hemoglobin present in a patient's liquid test sample is calculated by taking at least two diagnostic assay measurements of a patient's liquid test sample—e.g., total hemoglobin concentration and glycated hemoglobin concentration. The percent of glycated hemoglobin is calculated as the ratio of glycated hemoglobin concentration divided by the total hemoglobin concentration times 100%.

In order to calculate the percent glycated hemoglobin in a patient's liquid test sample, the total hemoglobin and the glycated hemoglobin component concentrations must be determined. Accordingly, one aspect of the presently disclosed and/or claimed inventive concept(s) comprises and/or consists of the creation and/or preparation of calibrators, calibration materials, and/or controls, as well as methods related thereto, for the calibration and calculation of total hemoglobin and/or glycated hemoglobin.

Non-Limiting Embodiments of the Presently Disclosed Inventive Concept(s) for the Preparation of Calibrators, Calibrator Materials, and/or Control Materials to Calibrate for High Levels of Percent Glycated Hemoglobin.

Figure 2:
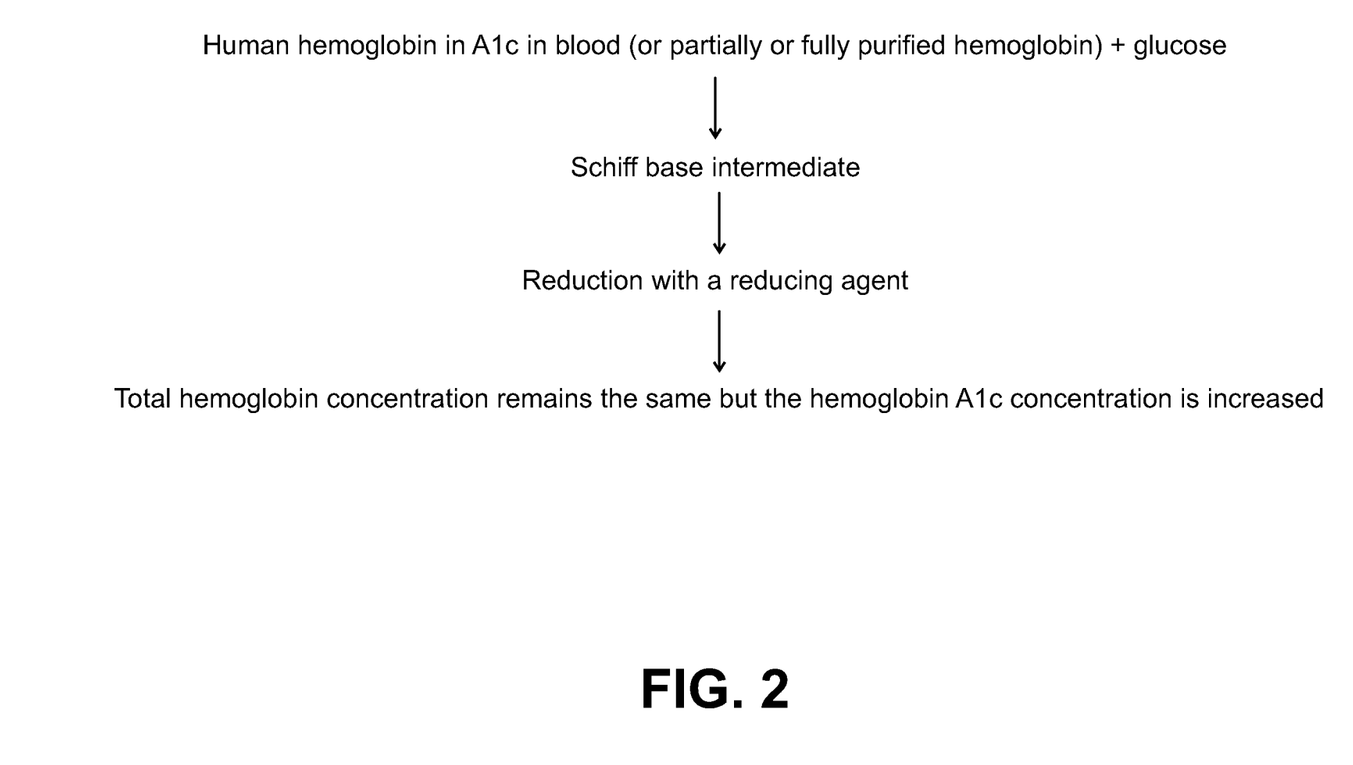
FIG. 2 is a flowchart of a non-limiting embodiment of a methodology for producing and/or preparing a highly-glycated hemoglobin calibrator in accordance with the presently disclosed and/or claimed inventive concept(s).

As shown in FIG. 2, in one non-limiting embodiment of the presently disclosed and/or claimed inventive concept(s), glycated hemoglobin present in an ex vivo blood sample or partially or fully-purified hemoglobin is reacted with a high concentration of exogenous glucose (i.e., greater than equal to about 200 nM of glucose) to produce, for instance, a Schiff base intermediate. The Schiff base intermediate is subsequently reduced by a reducing agent (such as, by way of example only, sodium borohydride and/or sodium cyanoborohydride) to produce a high amount and/or concentration of glycated hemoglobin, including, without limitation, up to an including about 25% glycated hemoglobin. The material containing the elevated concentration of glycated hemoglobin is then supplemented into human blood to increase the glycated hemoglobin concentration which is utilized to set the upper threshold of glycated hemoglobin in a calibrator(s), calibrator material(s), and/or control(s).

Figure 3:
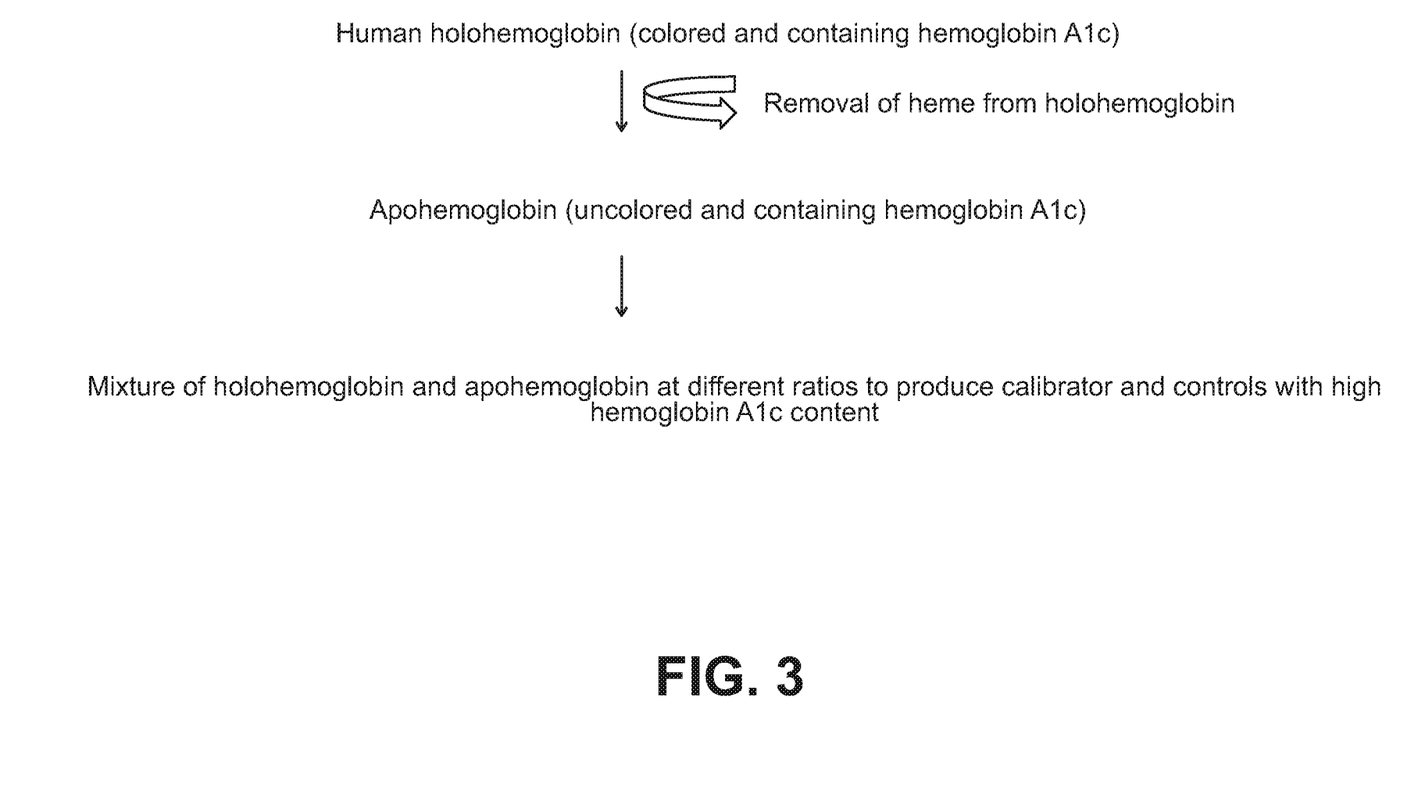
FIG. 3 is a flowchart of a non-limiting embodiment of a methodology for producing and/or preparing a highly-glycated hemoglobin calibrator via the removal of heme from hemoglobin in accordance with the presently disclosed and/or claimed inventive concept(s).

In another non-limiting embodiment of the presently disclosed and/or claimed inventive concept(s), and as shown in FIG. 3, hemoglobin's protein structure comprises four subunits (two α and two β) each containing an iron atom bound to a heme group (a colored iron-containing compound of the porphyrin class that form the non-protein portion of hemoglobin). Human apohemoglobin (the apoprotein of hemoglobin—i.e., the polypeptide portion of the conjugated hemoglobin protein) is produced which is colorless and contains glycated apohemoglobin. The heme groups can be removed from the apohemoglobin product via any methodology commonly known in the art, for instance, by way of example only, via precipitation of hemoglobin with cold acidic acetone followed by subsequent dialysis of the precipitate in a buffer. Addition of partially-glycated apohemoglobin to a calibrator, calibrator material, and/or control containing hemoglobin generates an increase in glycated hemoglobin measured by a diagnostic assay(s) since the signal generated by total hemoglobin in the assay is reduced. Accordingly, upper thresholds for glycated hemoglobin present in the calibrator(s), calibration material(s), and/or controls can be quantified and set for the conductance of hemoglobin-related diagnostic assays.

Figure 4:
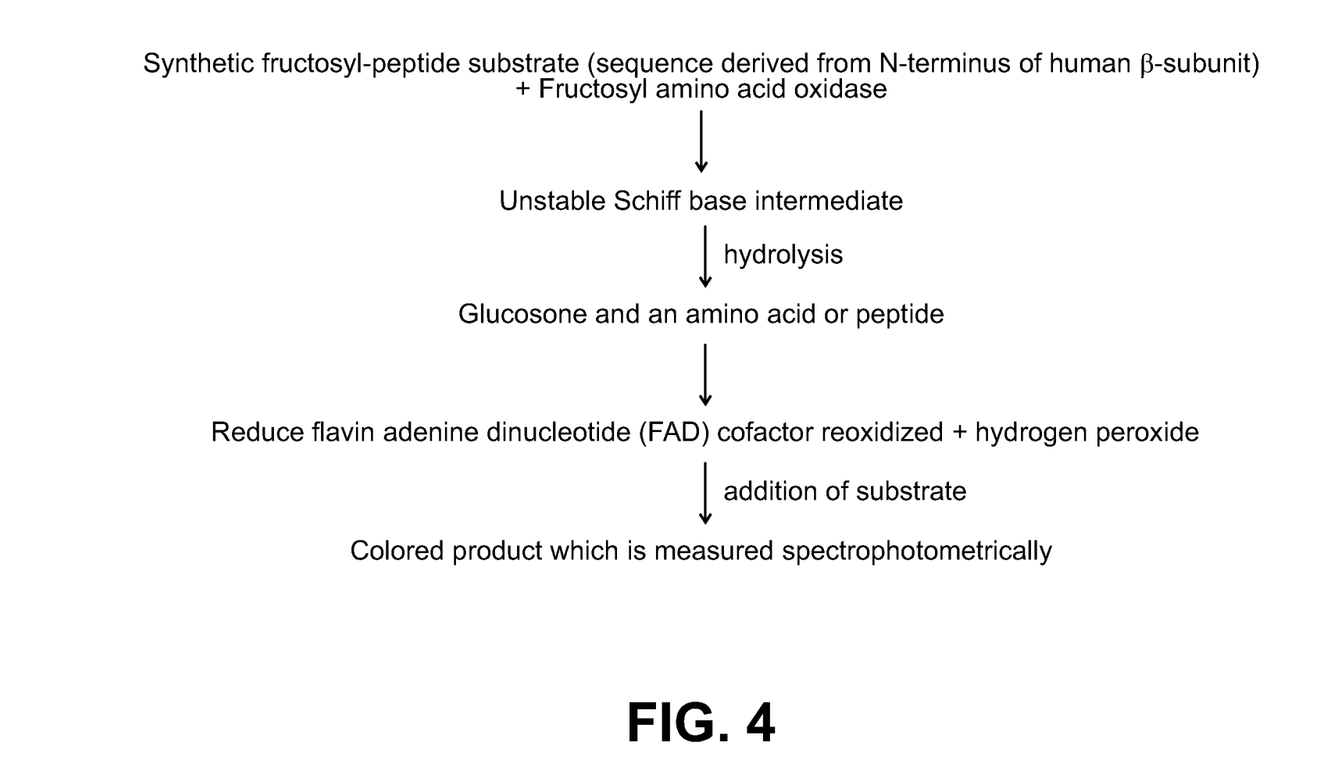
FIG. 4 is a flowchart of a non-limiting embodiment of a methodology for producing and/or preparing a highly-glycated hemoglobin calibrator utilizing a synthetic fructosyl-peptide substrate in accordance with the presently disclosed and/or claimed inventive concept(s).

Referring now to FIG. 4, shown therein is a non-limiting embodiment of a method for producing glycated hemoglobin calibrating materials and/or controls for enzymatic assays that employ fructosyl peptide oxidase. By way of example only, synthetic fructosyl-peptide (in which the sequence, in one non-limiting embodiment, is derived from the N-terminus of the human β-subunit) is used as a substrate for fructosyl amino acid oxidase. Some glycated hemoglobin enzyme-based detection assays utilize fructosyl amino acid oxidase (also referred to herein as fructosyl peptide oxidase or FPDX). These enzyme-based detection assays are advantageous and desirable because, among other things, they are rapid and reproducible.

FPDX catalyzes the oxidation of carbon-nitrogen bond(s) linking the C1 of the fructosyl moiety and the nitrogen of the amino group of fructosyl-containing amino acids. This reaction proceeds to an unstable Schiff base intermediate which hydrolyzes to produce glucosone and an amino acid and/or peptide. The FPDX's reduced flavin adenine dinucleotide (FAD) cofactor is then re-oxidized by molecular oxygen in solution which results in the release of hydrogen peroxide.

Current methods that utilize FPDX to measure the concentration of glycated hemoglobin employ a three-step process. First, hemoglobin is proteolytically digested. Next, the FPDX enzyme reacts with a fructosylated peptide to produce glucosone, an amino acid, and hydrogen peroxide. The final step involves the reaction of the hydrogen peroxide with a substrate to yield a colored product that is measured spectrophotometrically.

As previously disclosed herein, FPDX may be employed to measure and/or detect the concentration of glycated hemoglobin present in a patient's blood sample. In one non-limiting embodiment of the presently disclosed and/or claimed inventive concept(s), fructosyl-peptide is partially substituted for proteolyzed hemoglobin as the substrate for the aforementioned FPDX reaction. The use of glycated hemoglobin as a material to prepare a glycated hemoglobin calibrator, calibration material, and/or control provides an N-terminal glycated peptide (via proteolysis of hemoglobin) to FPDX to serve as a substrate for the production of hydrogen peroxide. By utilizing the synthetic substrate, the apparent glycated hemoglobin concentration is raised without affecting the total hemoglobin content, thereby increasing the percent of measured glycated hemoglobin for use as the upper threshold within the calibrator(s), calibrator material(s), and/or controls.

With respect to the synthetic substrate, in one non-limiting embodiment, the synthetic substrate may comprise and/or consist of fructosyl-valine and/or a fructosyl-valine-X, wherein X is a short peptide comprising and/or consisting of from about 2 amino acids to about 10 amino acids. In one non-limiting embodiment, the peptide sequence X is analogous to the N-terminal sequence of the human hemoglobin β-chain (such as, by way of example only, $NH_2$-Val-His-Leu-Thr-Pro-Glu-Glu-Lys-Ser-); however, a person having ordinary skill in the art should readily appreciate that the peptide sequence X may comprise and/or consist of any sequence that allows the fructosyl-peptide to serve and function as an effective substrate for FPDX. Accordingly, the calibrator material(s) created via this methodology comprise and/or consist of a combination of hemoglobin(s) which is needed to measure total hemoglobin and the peptide substrate.

Non-Limiting Embodiments of the Presently Disclosed Inventive Concept(s) for the Preparation of Calibrators, Calibrator Materials, and/or Control Materials to Calibrate for Low Levels of Percent Glycated Hemoglobin.

Figure 5:
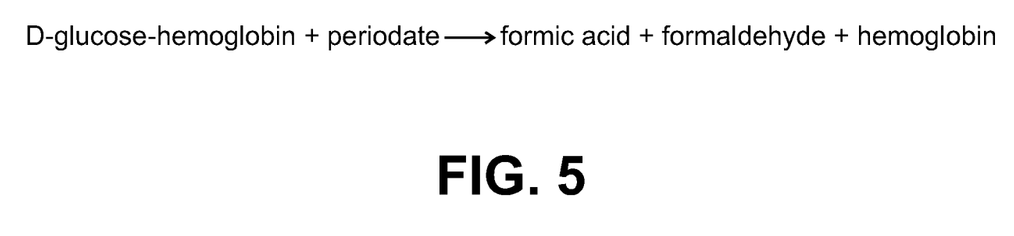
FIG. 5 is a flowchart of a non-limiting embodiment of a methodology for producing and/or preparing a reduced and/or low-glycated hemoglobin calibrator via the chemical modification of glycated hemoglobin by a periodate in accordance with the presently disclosed and/or claimed inventive concept(s).

As shown in FIG. 5, in one non-limiting embodiment of the presently disclosed and/or claimed inventive concept(s), calibrator(s), calibration material(s), and/or controls that contain a low level of percent glycated hemoglobin is/are created (including, without limitation, a level of percent glycated hemoglobin of about 0% glycated hemoglobin) by chemically modifying the fructose at the N-terminus of the hemoglobin β-chains. By way of example, and not by way of limitation, the low level of percent glycated hemoglobin comprises and/or consists of a range from about 0% to about 4%, or from about 0.5% to about 3.5%, or from about 1% to about 3%, or from about 1.5% to about 2.5%, or less than or equal to about 2%. Post modification, the fructose coupled to hemoglobin is chemically altered and no longer recognized by a glycated hemoglobin antibody or by FPDX or by phenylboronate groups. After the oxidation of glycated hemoglobin via at least one oxidant, for instance, by way of example only, periodate, the reaction can be quenched via the addition of a neutralizing chemical, such as, by way of example only, ethylene glycol. Following the quenching of the reaction, the mixture can be dialyzed or desalted via methodologies commonly known in the art to remove low molecular weight materials.

Figure 6:
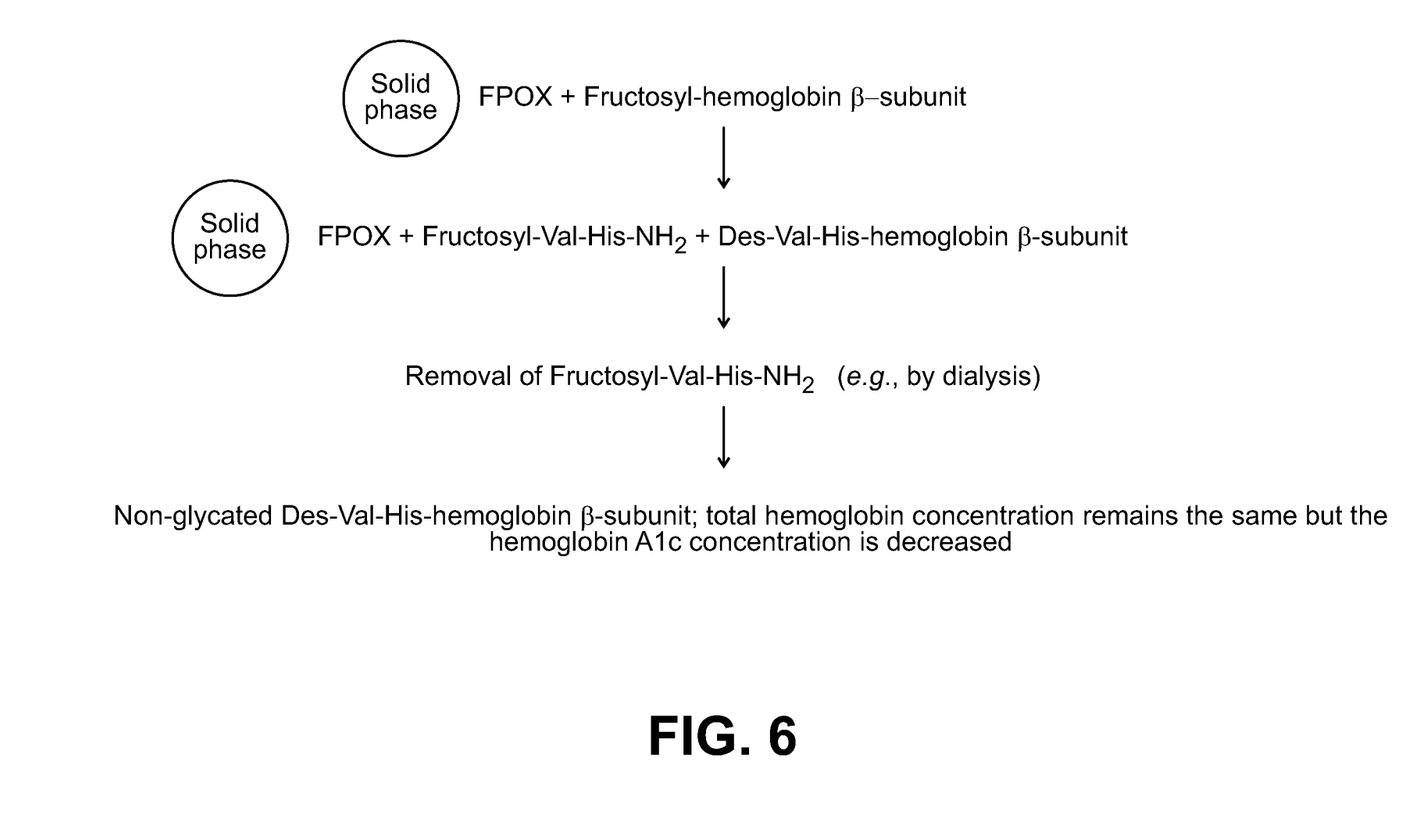
FIG. 6 is a flowchart of a non-limiting embodiment of a methodology for producing and/or preparing a reduced and/or low-glycated hemoglobin calibrator via utilization of a solid-phase enzyme in accordance with the presently disclosed and/or claimed inventive concept(s).

Referring now to FIG. 6, shown therein is a non-limiting embodiment of a method for producing calibrator(s), calibration material(s), and/or controls that contain and/or can detect low level of glycated hemoglobin present in a patient's liquid test sample. In this method, a solid phase (for instance, by way of example only, magnetic beads) coupled FPDX enzyme that proteolyzes hemoglobin β-subunits in hemolysates (products resulting from lysis/rupture of erythrocytes) between residues 2 and 3. Low molecular weight fructosyl-Val-His-$NH_2$ is then removed via dialysis or desalting methodologies commonly known in the art. The FPDX coupled beads are subsequently removed via, by way of example only, one or more magnets. The proteolytically truncated hemoglobin is then added to a normal preparation of hemoglobin, including, by way of example only, normal preparations of hemoglobin wherein the percent hemoglobin comprises and/or consists of a range of from about 4% to about 6.5%, or from about 4.5% to about 6%, or from about 5% to about 5.5%, or less than or equal to about 5.25%. Consequently, the total concentration of hemoglobin remains the same but the concentration of glycated hemoglobin is decreased.

Figure 7:
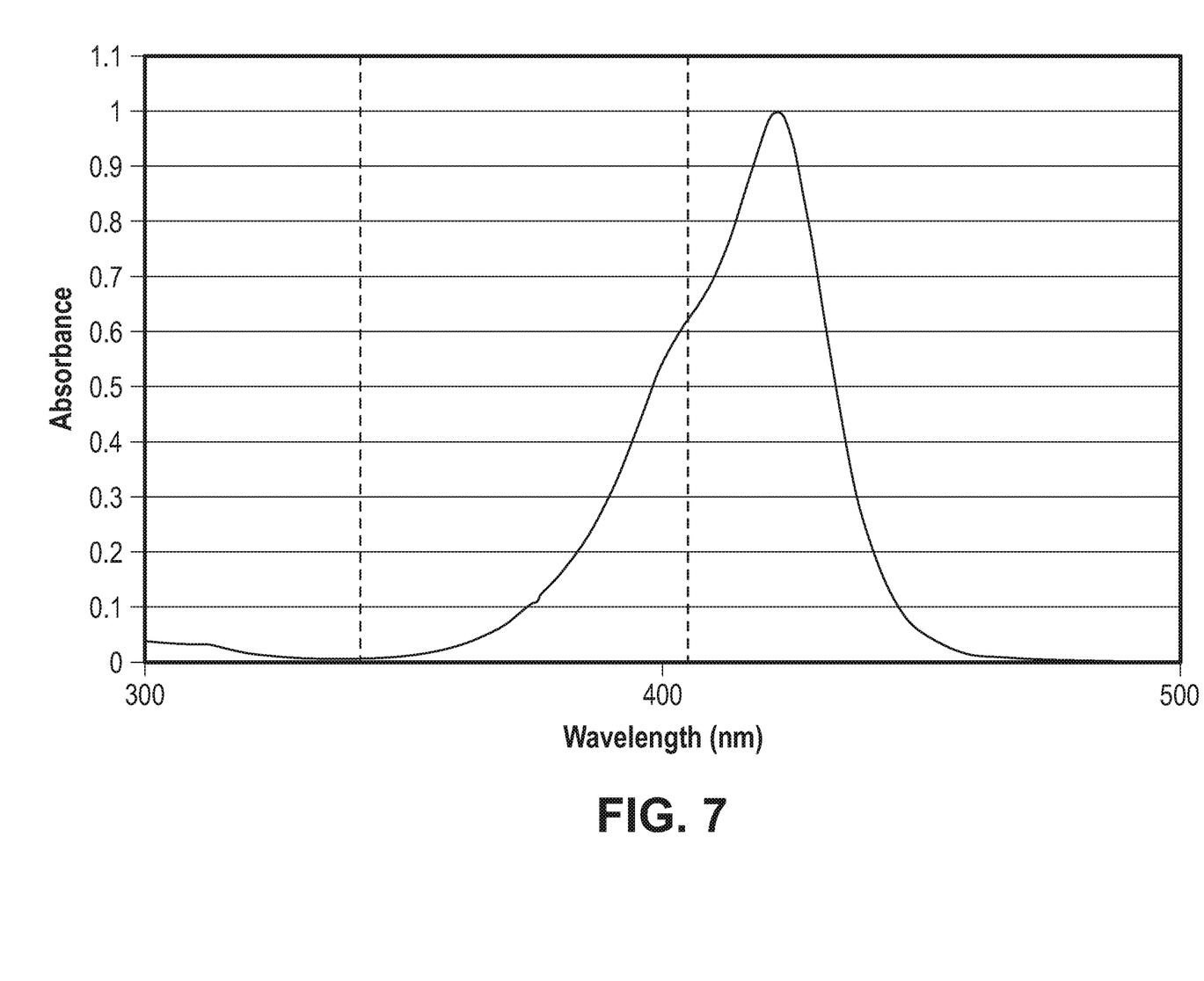
FIG. 7 is an absorbance spectrum of a dye associated with non-limiting embodiment of a methodology for producing and/or preparing a reduced and/or low-glycated hemoglobin calibrator via utilization of at least one dye in accordance with the presently disclosed and/or claimed inventive concept(s).

In another non-limiting embodiment of the presently disclosed and/or claimed inventive concept(s), calibrator(s), calibration material(s), and/or controls may be formulated with at least one dye or combination of dyes that have a desired spectral profile, such as, by way of example only, absorbance(s) in the spectral range of from about 400 nanometers to about 700 nanometers. With respect to percent glycated hemoglobin assays, the at least one dye absorbs at the wavelength(s) used to measure total hemoglobin in the assay, but does not absorb at the wavelength(s) used to measure either glycated hemoglobin or the assay blank. By way of example only, qualified dyes include any dyes that meet the criteria above, including, without limitation VIS423A and/or VIS433A commercially available for sale from QCR Solution Corp. For instance, as shown in FIG. 7, total hemoglobin is measured at about 405 nanometers, a wavelength absorbed by the at least one dye. The at least one dye, however, does not absorb at about 340 nanometers used to measure glycated hemoglobin or at about 700 nanometers used to blank the assay. This methodology results in a high reading for total hemoglobin and a normal reading for glycated hemoglobin thereby resulting in a low percent glycated hemoglobin value (i.e., a percent glycated hemoglobin value of less than about 4%).

Figure 8:
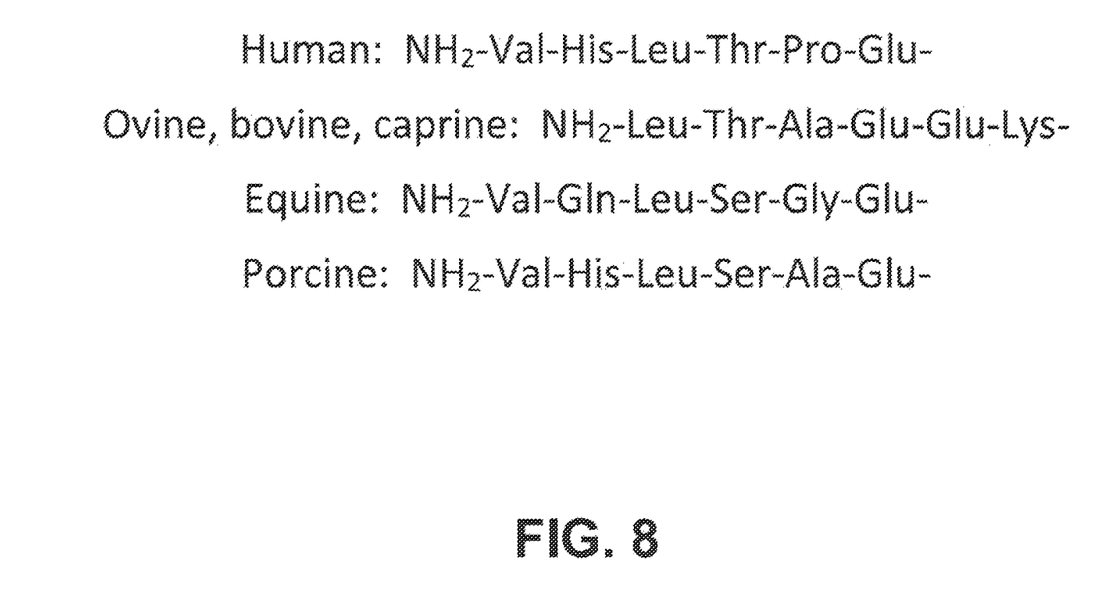
FIG. 8 is a non-exhaustive list of N-terminal amino acid sequences for humans and various animal hemoglobin β-subunits associated with a non-limiting embodiment of a methodology for producing and/or preparing a reduced and/or low-glycated hemoglobin calibrator via the mixing of human blood and the blood from at least one animal in accordance with the presently disclosed and/or claimed inventive concept(s).

In another non-limiting embodiment of the presently disclosed and/or claimed inventive concept(s), calibrator(s), calibration material(s), and/or control(s) for detecting and/or calibrating for low percent glycated hemoglobin thresholds may be prepared by mixing animal (such as, by way of example only, ovine, bovine, caprine, equine, porcine, and combinations thereof) blood with human blood. When an immunoassay is employed, the selected animal blood must not have an N-terminal amino acid sequence that cross-reacts with the anti-glycated hemoglobin antibody used in the immunoassay that binds to the N-terminus of glycated hemoglobin β-subunit(s). A non-limiting list of exemplary amino acid sequences utilized in accordance with the presently disclosed and/or claimed inventive concept(s) is detailed in FIG. 8. This methodology results in a near normal total hemoglobin assay result (i.e., from about 4% to about 5.6% glycated hemoglobin) and a low glycated hemoglobin result (i.e., less than about 4% glycated hemoglobin) thereby leading to a low percent glycated hemoglobin value.

In another non-limiting embodiment of the presently disclosed and/or claimed inventive concept(s), calibrator(s), calibration material(s), and/or control(s) for detecting and/or calibrating for low percent glycated hemoglobin thresholds may be prepared by depleting a portion or all of the glycated hemoglobin from total hemoglobin in a blood sample using a technique such as, by way of example only, cation-exchange chromatography and/or boronate affinity chromatography. The resulting product contain a normal amount of total hemoglobin with a reduced concentration of glycated hemoglobin, thereby resulting in a low percent glycated hemoglobin value, as described elsewhere herein.

Calibrator(s), calibration material(s), and/or controls created in accordance with the presently disclosed and/or claimed inventive concept(s) provide for distinct advantages, including, but not limited to: (i) calibrator(s) with a very low or very high percent glycated hemoglobin can be prepared; (ii) the presently disclosed and/or claimed methodologies (including, without limitation, the preparation of the calibrator(s), calibration material(s), and/or control(s) and methods of assay calibration) allow for the percent of glycated hemoglobin levels in such calibrator(s), calibration material(s), and/or controls to be equal to the lowest value and/or the highest value of percent hemoglobin found in human blood; (iii) the presently disclosed and/or claimed methodologies do not require changes to existing assay formats; and (iv) there is no requirement to search for blood specimens with a very low or very high percent glycated hemoglobin content (which can be difficult to find and obtain).

Non-Limiting Examples of the Inventive Concept(S)

A method for preparing a calibration system comprising at least two calibrators for use in an analyte detection assay instrument, the method comprising the steps of:
preparing a first calibrator, the first calibrator having a first concentration of an analyte of interest present in a patient's liquid test sample, wherein the first concentration is higher than an average threshold concentration of the analyte of interest present in the patient's liquid test sample; and preparing a second calibrator, the second calibrator having a second concentration of the analyte of interest present in the patient's liquid test sample, wherein the second concentration is lower than the average threshold concentration of the analyte of interest present in the patient's liquid test sample.

The method, wherein the patient's liquid test sample is whole blood.

The method, wherein the analyte of interest is selected from the group consisting of total hemoglobin, glycated hemoglobin, and combinations thereof.

The method, wherein the average threshold concentration of the glycated hemoglobin is from about 4% to about 8% of a concentration the total hemoglobin present in the patient's liquid test sample.

The method, wherein the first concentration of the glycated hemoglobin is equal to or greater than about 8.1%.

The method, wherein the second concentration of the glycated hemoglobin is equal to or less than about 3.9%.

The method, wherein the first concentration of the first calibrator is increased above the average threshold concentration of the glycated hemoglobin by a method selected from the group consisting of glucose addition and reaction, removal of heme, alteration via synthetic fructosyl-peptide substrate, and combinations thereof.

The method, wherein the synthetic peptide is an N-terminal fructosyl peptide.

The method, wherein the second concentration of the second calibrator is decreased below the average threshold concentration of the glycated hemoglobin by a method selected from the group consisting of chemical modification, utilization of at least one solid phase-bound enzyme, utilization of at least one dye, and combinations thereof.

The method, wherein the chemical modification comprises the oxidation of the glycated hemoglobin with periodate.

The method, wherein at least one solid phase-bound enzyme comprises fructosyl peptide oxidase bound to magnetic beads.

A method for calibrating at least one diagnostic assay utilizing a calibration system, the method comprising the steps of: performing at least two calibration measurements utilizing a calibration system present within a diagnostic assay instrument for the conductance of at least diagnostic assay, the calibration system comprising: a first calibrator, the first calibrator having a first concentration of an analyte of interest present in a patient's liquid test sample, wherein the first concentration is higher than an average threshold concentration of the analyte of interest present in the patient's liquid test sample; and a second calibrator, the second calibrator having a second concentration of the analyte of interest present in the patient's liquid test sample, wherein the second concentration is lower than the average threshold concentration of the analyte of interest present in the patient's liquid test sample; calculating a calibration curve utilizing the values obtained from the at least two measurements; and establishing numerical values for the first concentration and the second concentration to determine the accuracy of results obtained from the conductance of the at least one diagnostic assay.

The method, wherein the patient's liquid test sample is whole blood.

The method, wherein the analyte of interest is selected from the group consisting of total hemoglobin, glycated hemoglobin, and combinations thereof.

The method, wherein the average threshold concentration of the glycated hemoglobin is from about 4% to about 8% of a concentration of the total hemoglobin present in the patient's liquid test sample.

The method, wherein the first concentration of the glycated hemoglobin is equal to or greater than about 8.1%.

The method, wherein the second concentration of the glycated hemoglobin is equal to or less than about 3.9%.

Thus, in accordance with the presently disclosed and claimed inventive concept(s), there have been provided methods for preparing calibrator(s), calibration material(s), and/or controls used for calibrating at least one diagnostic assay. As described herein, the presently disclosed and claimed inventive concept(s) relate to embodiments of improved methods for that produce diagnostic assay calibrators, calibration materials, and/or controls that span the clinical assay range of percent glycated hemoglobin from very low (i.e., less than or equal to about 3%) to very high (greater than or equal to about 18%), as well as kits, devices, and methods of use related thereto. Accordingly, the present disclosed and/or claimed inventive concept(s) fully satisfy the objectives and advantages set forth hereinabove. Although the presently disclosed and claimed inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and claimed inventive concept(s).

What is claimed is:

1. A method for preparing a calibration system comprising at least two calibrators for use in an analyte detection assay instrument, wherein an analyte of interest is glycated hemoglobin, the method comprising the steps of:
   preparing a first calibrator, the first calibrator having a first concentration of glycated hemoglobin present in a patient's liquid test sample, wherein the first concentration is higher than an average threshold concentration of glycated hemoglobin present in the patient's liquid test sample; and
   preparing a second calibrator, the second calibrator having a second concentration of glycated hemoglobin present in the patient's liquid test sample, wherein the second concentration is lower than the average threshold concentration of glycated hemoglobin present in the patient's liquid test sample; and
   wherein the second concentration of the second calibrator is decreased below the average threshold concentration of glycated hemoglobin by a method selected from the group consisting of chemical modification, utilization of at least one solid phase-bound enzyme, utilization of at least one dye, and combinations thereof, and wherein at least one of:
      the chemical modification comprises oxidation of the glycated hemoglobin with periodate; or
      the at least one solid phase-bound enzyme comprises fructosyl peptide oxidase bound to magnetic beads.

2. The method of claim 1, wherein the patient's liquid test sample is whole blood.

3. The method of claim 1, wherein the average threshold concentration of glycated hemoglobin is in a range of from about 4% to about 8% of a concentration of total hemoglobin present in the patient's liquid test sample.

4. The method of claim 3, wherein the first concentration of glycated hemoglobin is equal to or greater than about 8.1%.

5. The method of claim 3, wherein the second concentration of glycated hemoglobin is equal to or less than about 3.9%.

6. The method of claim 1, wherein the first concentration of the first calibrator is increased above the average threshold concentration of glycated hemoglobin by a method selected from the group consisting of glucose addition and reaction, removal of heme, alteration via a synthetic fructosyl-peptide substrate, and combinations thereof.

7. The method of claim 6, wherein the synthetic fructosyl-peptide substrate is an N-terminal fructosyl-peptide substrate.

8. A method for calibrating at least one diagnostic assay for an analyte of interest utilizing a calibration system, the method comprising the steps of:
   performing at least two calibration measurements utilizing a calibration system present within a diagnostic assay instrument for conductance of at least one diagnostic assay for an analyte of interest, wherein the analyte of interest is glycated hemoglobin, the calibration system comprising:
      a first calibrator, the first calibrator having a first concentration of glycated hemoglobin present in a patient's liquid test sample, wherein the first concentration is higher than an average threshold concentration of glycated hemoglobin present in the patient's liquid test sample; and
      a second calibrator, the second calibrator having a second concentration of glycated hemoglobin present in the patient's liquid test sample, wherein the second concentration is lower than the average threshold concentration of glycated hemoglobin present in the patient's liquid test sample, wherein the second concentration of the second calibrator is decreased below the average threshold concentration of glycated hemoglobin by a method selected from the group consisting of chemical modification, utilization of at least one solid phase-bound enzyme, utilization of at least one dye, and combinations thereof, and wherein at least one of:
         the chemical modification comprises oxidation of the glycated hemoglobin with periodate; or
         the at least one solid phase-bound enzyme comprises fructosyl peptide oxidase bound to magnetic beads;
   calculating a calibration curve utilizing values obtained from the at least two calibration measurements; and
   establishing numerical values for the first concentration and the second concentration to determine accuracy of results obtained from conductance of the at least one diagnostic assay.

9. The method of claim 8, wherein the patient's liquid test sample is whole blood.

10. The method of claim 8, wherein the average threshold concentration of glycated hemoglobin is in a range of from about 4% to about 8% of a concentration of total hemoglobin present in the patient's liquid test sample.

11. The method of claim 10, wherein the first concentration of glycated hemoglobin is equal to or greater than about 8.1%.

12. The method of claim 10, wherein the second concentration of glycated hemoglobin is equal to or less than about 3.9%.

13. The method of claim 8, wherein the first concentration of the first calibrator is increased above the average threshold concentration of glycated hemoglobin by a method selected from the group consisting of glucose addition and reaction, removal of heme, alteration via a synthetic fructosyl-peptide substrate, and combinations thereof.

14. The method of claim 13, wherein the synthetic fructosyl-peptide substrate is an N-terminal fructosyl-peptide substrate.

* * * * *